United States Patent [19]

Swanson

[11] 4,228,238

[45] Oct. 14, 1980

[54] METHOD OF LABORATORY TESTING IN WATER-BASED CULTURE MEDIA FOR ZONES OF INHIBITION

[75] Inventor: Damon Swanson, Denver, Colo.

[73] Assignee: The Allor Foundation, Boston, Mass.

[21] Appl. No.: 68,751

[22] Filed: Aug. 23, 1979

[51] Int. Cl.³ .............................................. C12K 1/04
[52] U.S. Cl. ...................................... 435/32; 435/33; 435/36
[58] Field of Search ............................. 435/32, 33, 36

[56] References Cited

U.S. PATENT DOCUMENTS

| | | | |
|---|---|---|---|
| 3,126,325 | 3/1964 | Poole | 435/32 |
| 3,597,321 | 8/1971 | Kronish et al. | 435/36 |
| 3,992,523 | 11/1976 | Loud et al. | 435/171 |
| 4,168,206 | 9/1979 | Boyer | 435/32 |

*Primary Examiner*—Benoit Castel
*Attorney, Agent, or Firm*—Rines and Rines, Shapiro and Shapiro

[57] ABSTRACT

This disclosure is concerned with providing extractions of oil-based anti-microbial materials, such as essential oil extracts and the like, that can be rendered miscible with water-based culture media with which they are otherwise non-miscible, to enable zone of inhibition testing with such culture media.

3 Claims, No Drawings

METHOD OF LABORATORY TESTING IN WATER-BASED CULTURE MEDIA FOR ZONES OF INHIBITION

The present invention relates to methods of zone of inhibition laboratory testing, being more particularly concerned with the problems underlying the application of oil-based anti-microbial herbal extracts and the like, such as essential oils and similar derivatives, contained in oil or similar bases, non-miscible with water-based culture media, such as various agars and the like, and thus incapable of showing their actual anti-microbial effects in conventional zone of inhibition and related culture testing.

While the anti-microbial properties of oil-based extracts, such as essential oils and the like, can be demonstrated by the results of in vivo testing, it is sometimes desirable to obtain a laboratory indication of efficacy, as for rapidly determining the efficacy of a newly manufactured batch; and it is further desirable to do so with well-known zone of inhibition type techniques employing incubated agar plate or similar cultures and sensitivity discs, as described, for example, in U.S. Pat. No. 3,992,523, of the Allor Foundation, the assignee of the present invention. As before stated, this has not heretofore been reliably possible in view of the non-miscible character of the water-based cultures and the oil-based active materials.

An object of the present invention, accordingly, is to provide a new and improved method of zone of inhibition culture testing that obviates such problems and enables the testing of oil-based anti-microbial materials with water-based cultures.

A further object is to provide a novel zone of inhibition testing process of more general utility as well.

Other and further objects are explained hereinafter and are more particularly delineated in the appended claims. In summary, however, from one of its important aspects, the invention embraces a method of enabling zone of inhibition testing of oil-based anti-microbial materials and the like with non-miscible oil-based culture media and the like, that comprises, mixing said oil-based anti-microbial materials with an alcohol that, in relatively dilute concentration, does not demonstrate substantial anti-microbial activity, to form an emulsion containing an extraction of the said materials; diluting the alcohol emulsion with water sufficient to bring the alcohol to said relatively dilute concentration of non-anti-microbial activity; saturating a sensitivity disc with a sample of the diluted emulsion after contacting the disc with a water-based culture medium; evaporating the alcohol saturated into the disc; inverting and incubating the culture medium carrying the disc; and observing zones of inhibition produced on the disc as a result of miscible reaction with the water-based culture medium of the alcohol-extracted, originally non-miscible, oil-based anti-microbial materials. Preferred or best mode embodiments are hereinafter presented.

Underlying the invention is the finding that there are certain alcohols useable for extraction functions, such as ethanol and methanol, that in large percentage concentration can affect bacteria and the like, but that, in more diluted form, are substantially ineffective against bacteria. In the specific and preferred case of ethanol, for example, 95% ethanol can show bacterial inhibition in zone of inhibition testing; but 50% ethanol does not produce such an indication.

The process of the invention, accordingly, involves obtaining, in the illustrative example of ethanol, an ethanol extraction of the essential oil or similar extracts that can be rendered miscible with water-based culture media and the like and that utilizes sufficiently dilute ethanol to avoid any substantial effect of the same upon the culture. In this manner, following evaporation of the ethanol suspension, the water-miscible essential oil extraction or the like, can interact with the incubated culture medium showing regions of zones or zones of anti-microbial inhibition on sensitivity discs contacting the culture plate.

EXAMPLE 1

A preferred example for use with mineral oil-based essential extracts, including chamazulene, is as follows. To an aliquot of 95% ethanol (ca 2.5 ml), add twice the volume of oil extract (ca 5.0 ml) in a stoppered container and shake for a few minutes. Allow the oil/ethanol layers to separate by, for example, standing overnight. A small amount of oil will be retained as an emulsion with the ethanol even after prolonged standing. The odor of essential oils will be noted in the ethanol layer.

A specific volume of the ethanol is drawn off and diluted with an equal volume of water. The ethanol has now been diluted to slightly less than 50% concentration, before described, while the potential essential oil concentration has remained constant. A white emulsion forms when water is added to the ethanol, presumably from the mineral oil carry-over into ethanol.

A control of straight mineral oil/ethanol extraction may be run in parallel, being treated in the same manner as the extracts being tested.

By drawing off 20 microliters of the 50% ethanol extractions (active ingredients and control), the same is applied to saturate a sensitivity disc which has been placed on a previously inoculated agar plate, as is well-known and discussed, for example, in said Letters Patent. Suitable agars include water-based Trypticase Soy, maltose extract and Czapek solution agars. The ethanol suspension is then allowed to evaporate. The plate is now inverted and the culture incubated at a specified temperature generally for 24 and 48 hours, noting zones of inhibition at each time.

In this manner, mineral-oil-based essential oil extracts including chamazulene have been successfully zone-measured for anti-microbial efficacy in gram positive Staphylococcus albus cultures in Trypticase Soy agar, to which the addition of non-ethanol-extracted samples produced no zone of inhibition effects as a result of the lack of miscibility previously discussed.

EXAMPLE 2

As a second example, the above process of Example I was also successfully employed to produce zone of inhibition effects against a gram negative culture of Escherichia coli, also in the agar medium of Example I.

EXAMPLE 3

The process of the preceding examples was also repeated for active oil extracts including thujone, indicating antimicrobial properties against agar cultures of Staphylococcus albus and Escherichia coli.

EXAMPLE 4

As still another example, the process delineated in Example I can be employed with a somewhat less than 50% extraction solution of methanol, instead of ethanol.

Clearly other alcohol or alcohol-like extraction solutions having properties similar to ethanol may be used; as may other water-based or water-containing culture media containing other cultures than the exemplary illustrations above discussed.

Further modifications will occur to those skilled in this art and such are considered to fall within the spirit and scope of the invention as defined in the appended claims.

What is claimed is:

1. A method of enabling zone of inhibition testing of essential oil extracts with non-miscible oil-based culture media and the like, that comprises, mixing said essential oil extracts with an alcohol that, in relatively dilute concentration, does not demonstrate substantial anti-microbial activity, to form an emulsion containing an extraction of the same materials; diluting the alcohol emulsion with water sufficient to bring the alcohol to said relatively dilute concentration of non-anti-microbial activity; saturating a sensitivity disc with a sample of the diluted emulsion after contacting the disc with a water-based culture medium; evaporating the alcohol saturated into the disc; inverting and incubating the culture medium carrying the disc; and observing zones of inhibition produced on the disc as a result of miscible reaction with the water-based culture medium of the alcohol-extracted originally non-miscible essential oil extracts.

2. A method as claimed in claim 1 in which said essential oil extracts are anti-microbial materials.

3. A method as claimed in claim 1 and in which said alcohol is ethanol and said relatively dilute concentration is less than about 50%.

* * * * *

UNITED STATES PATENT AND TRADEMARK OFFICE
CERTIFICATE OF CORRECTION

PATENT NO. : 4,228,238
DATED : October 14, 1980
INVENTOR(S) : Damon Swanson

It is certified that error appears in the above-identified patent and that said Letters Patent are hereby corrected as shown below:

IN THE SPECIFICATION:

Column 1:

line 42, change "oil-based" to -- water-based --.

IN THE CLAIMS:

Claim 1:

line 2, change "oil-based" to -- water-based --.

Signed and Sealed this

Seventh Day of April 1981

[SEAL]

Attest:

RENE D. TEGTMEYER

Attesting Officer     Acting Commissioner of Patents and Trademarks